United States Patent [19]

Zaiger

[11] Plant 4,508

[45] Mar. 4, 1980

[54] PEACH TREE

[76] Inventor: Chris F. Zaiger, 537 Rosemore Ave., Modesto, Calif. 95351

[21] Appl. No.: 774

[22] Filed: Dec. 19, 1978

[51] Int. Cl.[2] ..... A01H 5/03

[52] U.S. Cl. ..... Plt./43

[58] Field of Search ..... Plt./43

*Primary Examiner*—Robert E. Bagwill

[57] ABSTRACT

A new and distinct variety of peach tree which is of large size, vigorous and upright in growth; the tree being a regular and productive bearer of large, firm, yellow flesh, freestone fruit of high red skin color, with excellent eating and shipping quality in the late maturing season.

No Drawings

ORIGIN OF THE VARIETY

The present variety of peach tree was originated by me in my experimental orchard located at Modesto, Calif., as an open pollenated seedling of O'Henry Peach (U.S. Plant Pat. No. 2,964). These seedlings were grown and maintained under close observation by me and the present variety which evidenced distinctive desirable characteristics was selected for asexual reproduction and commercialization.

ASEXUAL REPRODUCTION OF THE VARIETY

The present variety of peach tree was asexually reproduced by budding, as performed by me, in my experimental orchard located at Modesto, Calif., shows that said characteristics come true to form and are established and transmitted through succeeding propagation.

SUMMARY OF THE VARIETY

The present variety of peach tree is of large size, vigorous, upright growth; which is a regular and productive bearer of large, firm, yellow flesh, freestone fruit, with an attractive red skin color and excellent eating and shipping quality; the fruit is further characterized by having fruit that colors two to three weeks before ripening and having a more attractive high red skin color than other peaches in the late maturing season ripening two weeks after O'Henry Peach (U.S. Plant Pat. No. 2,964).

BRIEF DESCRIPTION OF THE DRAWING

The accompanying photographic illustrations show typical specimens of the foliage and fruit of my new variety, an exterior and sectional view of the fruit with the stone in place and the section of a branch with the upper and lower surface of the foliage being illustrated. The photographs were taken shortly after being picked at maturity (shipping ripe) and the colors are as nearly true as reasonably possible in a color representation of this type.

DESCRIPTION OF THE VARIETY

The following is a detailed botanical description of the new and distinct variety of peach tree and its fruit, with color definitions (except those in common terms) referenced to Reinhold Color Atlas, by A. Korneruf and J. H. Wanscher as based upon observations of specimens grown at Modesto, Calif.

Tree:
- *Size.*—Large.
- *Vigor.*—Vigorous.
- *Productivity.*—Productive.
- *Bearer.*—Regular.

Trunk:
- *Size.*—Medium stocky.
- *Texture.*—Medium shaggy.

Branches:
- *Size.*—Medium stocky.
- *Texture.*—Smooth to medium rough.
- *Color.*—Brown to grayish brown.
- *Lenticels.*—Medium size, medium quantity.

Leaves:
- *Size.*—Large. Average length — 7". Average width — 1½".
- *Form.*—Lanceolate, acutely pointed.
- *Thickness.*—Medium.
- *Margin.*—Crenate.
- *Petiole.*—Average length — 9/16". Average width — 3/32".
- *Gland.*—Average number 4, range 2 to 6. Reniform. Positioned on lower part of leaf blade and upper part of petiole.
- *Color.*—Upper surface — deep green (27-F-6 to 28-F-7). Lower surface — grayish green (28-E-6 to 28-E-7).

Flower buds:

*Size.*—Medium to large.
*Form.*—Plump.
*Pubescence.*—Pubescent.

Flowers:
*Size.*—Large — showy.
*Blooming period.*—Feb. 27, 1977 to Mar. 10, 1977. Varies sightly with climatic conditions.
*Pollen.*—Present.
*Color.*—Pink.

Fruit:
*Maturity when described.*—Hard ripe.
*Date of first picking.*—Aug. 29, 1977.
*Date of last picking.*—Sept. 5, 1977.
*Size.*—Large. Average diameter axially — 2⅞" to 3⅛". Average transversely in suture plane — 2¾" to 3".
*Form.*—Globose — nearly symmetrical.
*Suture.*—Shallow.
*Ventral surface.*—Nearly round — some slightly lipped.
*Apex.*—Rounded to slightly retuse.
*Base.*—Retuse.
*Cavity.*—Round. Average depth — ½". Average width — 11/16".

Skin:
*Thickness.*—Medium.
*Texture.*—Tenacious to flesh when firm ripe. Free when soft ripe.
*Tendency to crack.*—None.
*Down.*—Moderate. Medium length.
*Color.*—Bright yellow ground color — (4-A-8 to 5-A-8) overspread with red — (8-A-8 to 9-B-8).

Flesh:
*Color.*—Dark yellow (4-A-8) to cadmium orange (5-A-8), with red (9-B-8) near stone. Surface of pit cavity — red, with yellow fibers.
*Texture.*—Firm.
*Fibers.*—Few, tender.

*Amygdalin.*—Undetected.
*Ripens.*—Evenly.
*Flavor.*—Mild.
*Juice.*—Moderate.
*Aroma.*—Moderate.
*Eating quality.*—Excellent.

Stone:
*Type.*—Freestone.
*Size.*—Large. Average length — 1 7/16". Average width — 1". Average thickness — 9/16".
*Form.*—Ovid.
*Base.*—Mostly straight.
*Apex.*—Acuminate.
*Sides.*—Equal to unequal.
*Surface.*—Furrowed toward apex and pitted toward base.
*Ridges.*—Rounded.
*Tendency to split.*—Very slight.
*Color.*—Light brown.

Use: Local and long distance markets. Dessert.
Keeping quality: Excellent.
Shipping quality: Excellent.

The present variety of peach tree and its fruit herein described as grown by me at my experimental orchard at Modesto, Calif., the variety may vary in slight detail due to different climatic, soil conditions and cultural practices.

I claim:

1. A new and distinct variety of peach tree as described and illustrated, characterized by its large size, vigor, upright growth; and being a regular and productive bearer of large, firm, yellow flesh, freestone fruit with excellent eating and shipping quality; it is further characterized by having fruit that colors two to three weeks before maturity and having a more attractive red skin color than other late season varieties, ripening two weeks after O'Henry Peach (U.S. Plant Pat. No. 2,964).

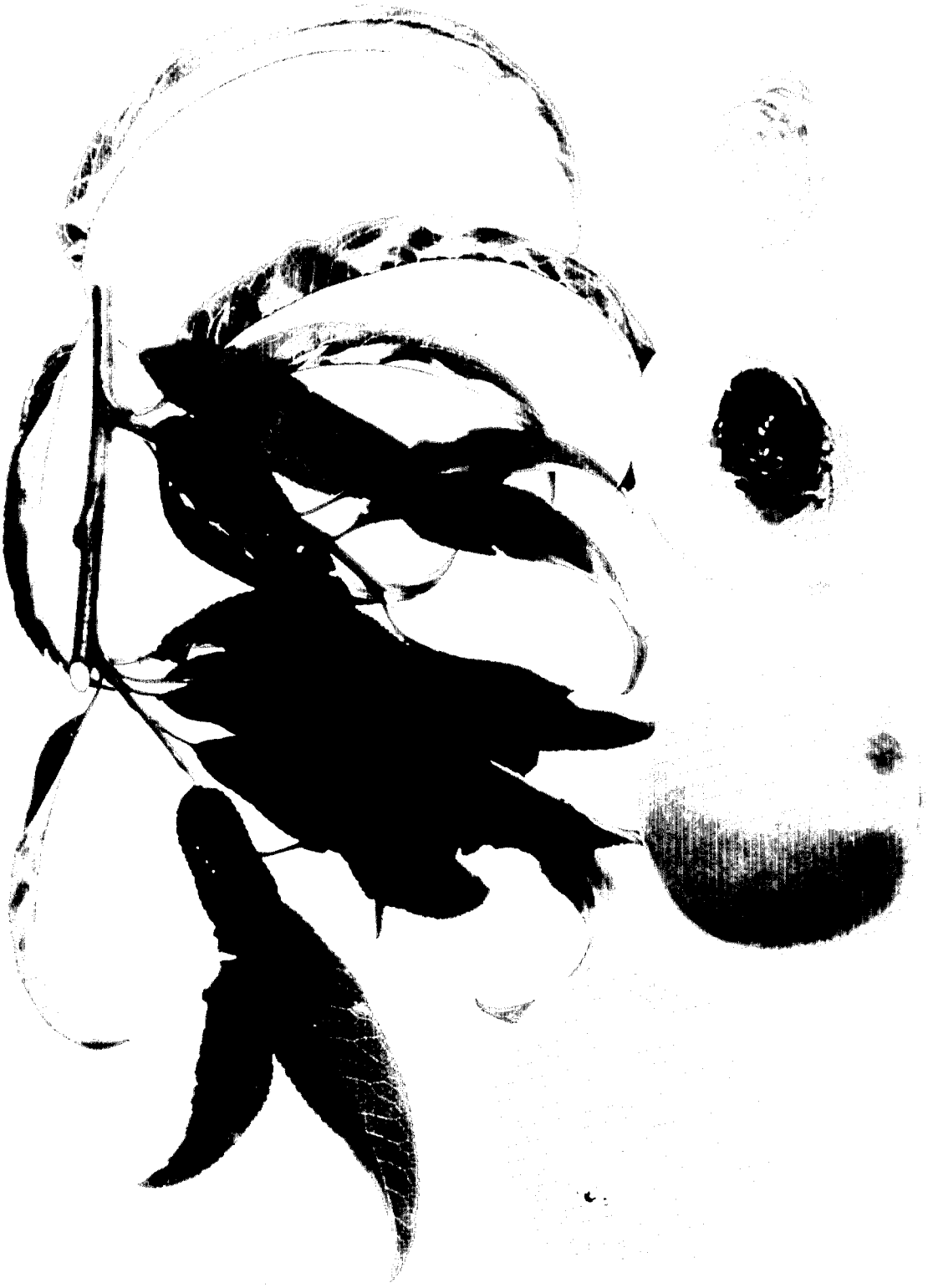

* * * * *